United States Patent

Bowser

[11] 4,003,713
[45] Jan. 18, 1977

[54] MULTIPLE TEST TUBE EVAPORATOR

[76] Inventor: Everett N. Bowser, 715 N. Main St., Glen Ellyn, Ill. 60137

[22] Filed: Aug. 14, 1975

[21] Appl. No.: 604,557

[52] U.S. Cl. ............................ 23/292; 23/259;
159/22; 159/DIG. 16; 312/209; 34/92
[51] Int. Cl.² ................................ B10L 3/00
[58] Field of Search ...... 159/22, DIG. 11, DIG. 16;
312/209, 1, 31.1; 34/92; 23/259, 292; 211/71, 74

[56] References Cited

UNITED STATES PATENTS

| 1,188,146 | 12/1915 | Bagley | 211/74 |
|---|---|---|---|
| 3,752,651 | 8/1973 | Bush | 23/259 |
| 3,836,329 | 9/1974 | Jordan | 23/292 |

FOREIGN PATENTS OR APPLICATIONS 674,883  11/1964  Italy ........................ 206/510

*Primary Examiner*—Norman Yudkoff
*Assistant Examiner*—Martin G. Mullen
*Attorney, Agent, or Firm*—Edward C. Threedy

[57] ABSTRACT

An apparatus for effecting evaporation of the contents of a multitude of containers, such as test tubes, including a rack and a manifold having multiple paths of open communication with a plurality of containers positioned within the rack, through which evaporation of the contents of the containers by vacuum or positive gas flow is achieved.

5 Claims, 6 Drawing Figures

MULTIPLE TEST TUBE EVAPORATOR

SUMMARY OF THE INVENTION

The apparatus for effecting evaporation of the contents of a multitude of containers comprises a generally rectangularly shaped rack having a pair of end walls between which extend a plurality of apertured supports as well as a bottom wall. The supports are formed to provide a series of axially aligned openings formed therein having like alignment with corresponding concave sockets formed in the surface of the bottom wall.

A manifold is adapted to snap between the upper free edges of the end walls so as to be disposed in a parallel plane with respect to the supports. The bottom wall surface of the manifold is formed to provide a plurality of concave seats each of which at its apex has pressure-fitted therein the base of an evaporator needle such that each needle will have open communication with the chamber of the manifold and is of such length as to be inserted into a container held within the rack.

GENERAL DESCRIPTION

The invention will be best understood by reference to the accompanying drawings, wherein the preferred form of embodiment is shown. In such drawings.

The multiple test tube evaporator comprises a rack 10 preferably constructed of a suitable plastic material and, as such, includes a bottom wall 11, the opposite ends of which support vertically extending end walls 12 and 13. Fixedly attached to the inner wall surfaces of the end walls 12 and 13 and extending in spaced parallel relation to the bottom wall 11, are supports 14 and 15.

Figure 4:
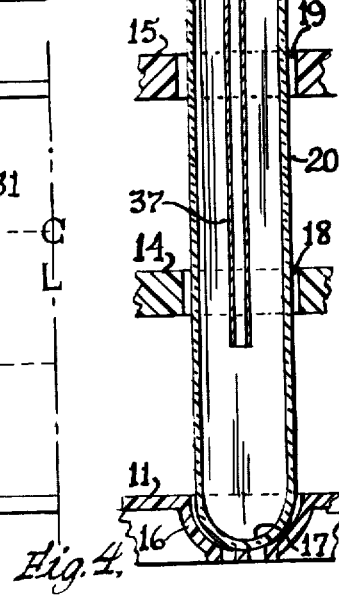
FIG. 4 is a fragmentary detailed sectional view showing the parts of the invention in operative relation.

Referring to FIG. 4, it is shown in detail that the bottom wall 11 of the rack 10 is provided with a concave seat 16, which has an open webbed bottom 17. In the supports 14 and 15 are formed axially aligned openings 18 and 19, respectively. By this arrangement the bottom wall 11 as well as the supports 14 and 15 will receive and hold in a relatively fixed vertical position an enlongated container, such as a test tube 20.

It should be noted that the uppermost support 15 is connected to the inner wall surface of the end walls 12 and 13 at a point approximately midway of the height of the end walls. By this construction the upper edges 21 and 22 of the end walls 12 and 13, respectively, have a resiliency resulting not only from the construction of the rack 10, but also from the material from which it is made, so that such upper edges 21 and 22 may be slightly separated so as to have snapped therebetween a manifold plate 23. This manifold plate 23 comprises a substantially flat top wall 24. The underside of the top wall 24 is formed to provide a peripheral shoulder 25 forming therein a recessed chamber 26.

Adapted to be mounted beneath the top wall 24 is a carrier plate 27. This carrier plate 27 is of a size such that it will rest upon the peripheral shoulder 25 formed on the underside of the top wall 24 so as to cooperate therewith to form the bottom closure for the chamber 26. The underside of the top wall 24 is provided with a plurality of square bosses 28 through which connecting screws 29 are adapted to be projected so as to be threadably received in tapped holes 20 formed in the carrier plate 27.

Figure 5:
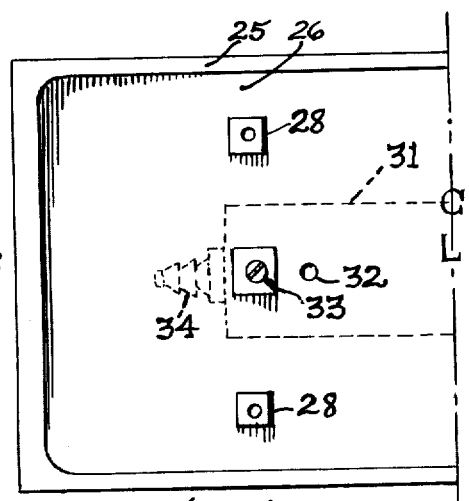
FIG. 5 is a fragmentary bottom plan view of the manifold chamber.

Mounted upon the exposed top surface of the top wall 24 is a hollow intake block 31 which is provided with a pair of openings formed therethrough which have open communication with like openings 32 formed through the top wall 24 and which provide communication with the chamber 26. The intake block 31 is connected to the top wall 24 by a series of screws 33, as shown in FIG. 5. The intake block 31 is provided with a suitable friction connector 34 to which a supply hose (not shown) may be connected.

Referring again to FIG. 4, it is there shown that the carrier plate 27 has its under surface formed to provide a plurality of conically shaped recesses 35 which, at their apexes, each have communication with a passage 36 extending through the carrier plate 27 so as to have open communication with the chamber 26. Press-fitted into each of the passages 36 is an evaporating needle 37.

Figure 1:
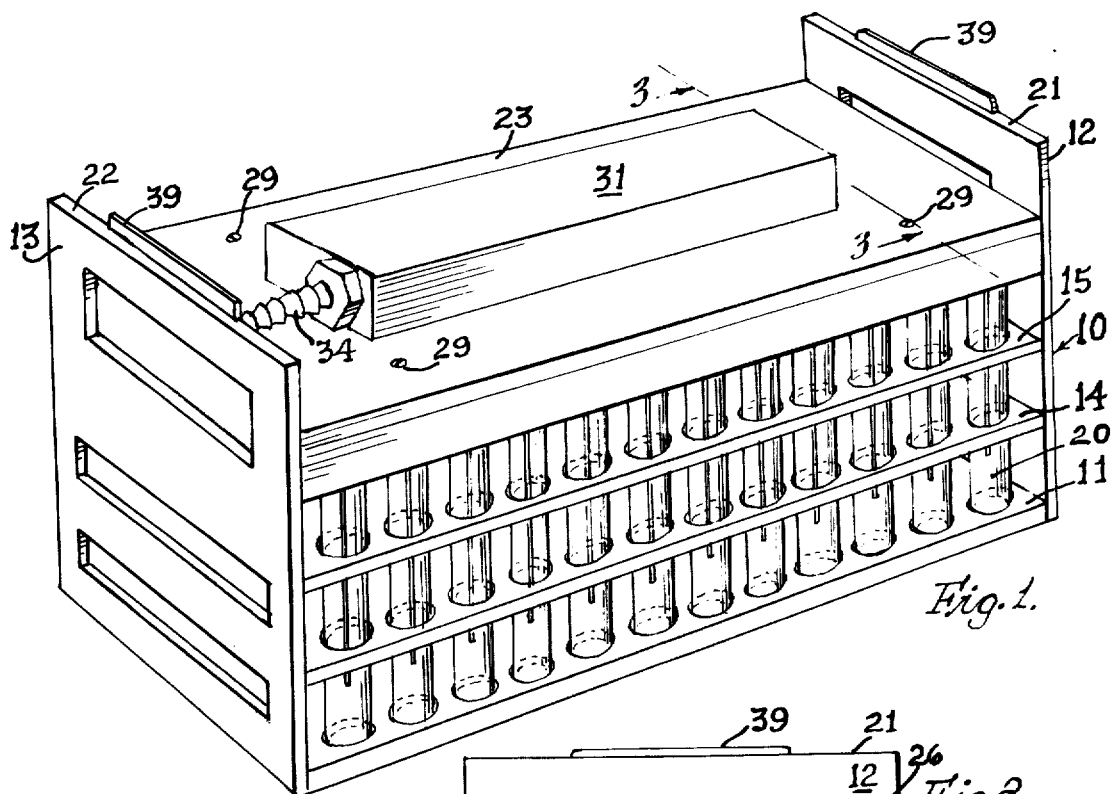
FIG. 1 is a perspective view of the multiple test tube evaporator.

From the foregoing description, it is apparent that when a plurality of containers, such as test tubes 20, are placed within the rack 10 so as to have their curved bases positioned within the concave seats 16 formed in the bottom wall 11 and extending vertically therefrom through the aligned openings 18 and 19 formed in the supports 14 and 15, respectively and with the manifold plate 23 snapped between the end walls 12 and 13 (see FIG. 1), the evaporating needles 37 will extend into the interior of the test tubes 20, as shown in FIG. 4. Through the presence of the conically shaped recesses 35, the upper circular edge of the test tubes 20 will seek its own seating within its respective recess 35 so as to effect a proper semi-closure of each tube.

When an ordinary vacuum line is connected to the connector 34 of the intake block 31, a vacuum will be created through the manifold 23 and effect evaporation of the contents of each of the test tubes 20 so as to effect evacuation therefrom. Through the use of the device, either positive or negative air pressures may be supplied through the manifold to effect the evaporation process. The rack may, if required, be subjected to temperature control achieved through either a liquid bath or suitable refrigeration. By reason of the fact that the rack is fabricated from plastic, such as polyurethane, it is resistant to a variety of organic solvents.

Figures 2, 3:
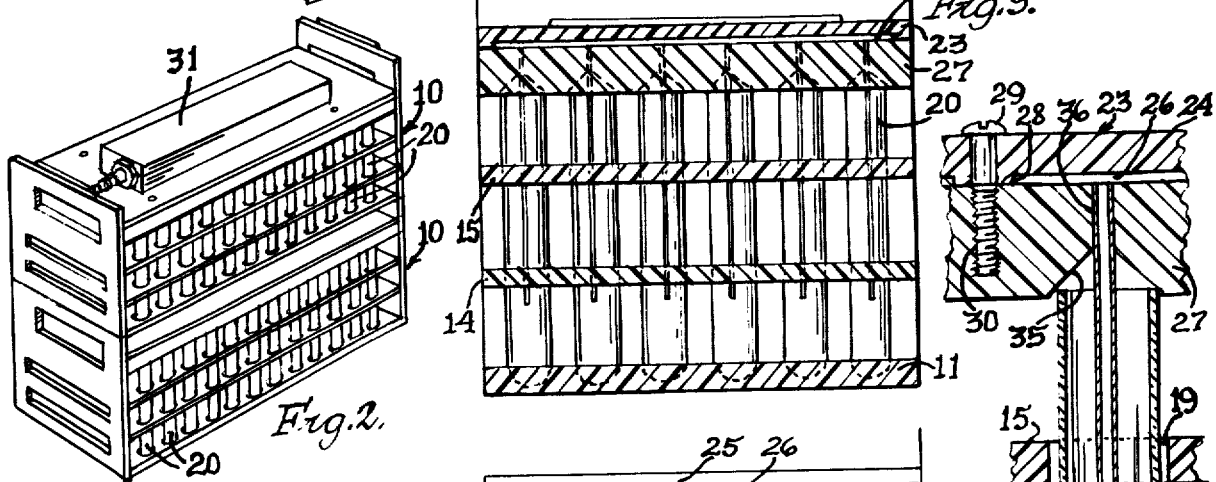
FIG. 2 is a perspective view of a pair of stacked multiple test tube evaporators.
FIG. 3 is a detailed sectional view taken on line 3—3 of FIG. 1.
Figure 6:
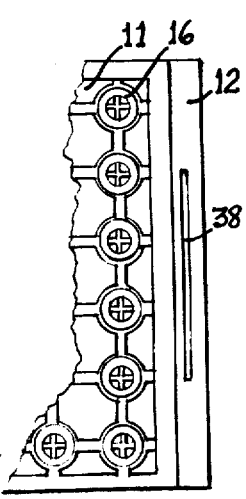
FIG. 6 is a fragmentary bottom plan view of the base of the evaporator.

Referring to FIG. 6, it is noted that each of the bottom surfaces of the end walls 12 and 13 may be slotted as at 38 for the purpose of receiving partial tabs 39 formed on opposite upper edges 21 and 22 of the end walls 12 and 13, so that the racks may be stacked vertically, as shown in FIG. 2.

While I have illustrated and described the preferred form of construction for carrying my invention into effect, this is capable of variation and modification without departing from the spirit of the invention. I, therefore, do not wish to be limited to the precise details of construction set forth, but desire to avail myself of such variations and modifications as come within the scope of the appended claims.

I claim:
1. A multiple test tube evaporator comprising
   a. a rack having a substantially rectangularly shaped bottom wall and upstanding end walls,
   b. supports extending between said end walls below a midline therethrough so as to permit the upper portions of said end walls to be yieldably separable,
   c. means provided by said bottom wall for receiving the closed end of a test tube,
   d. means provided by said supports, in vertical alignment with said receiving means provided by said bottom wall, retaining said test tubes in a perpendicular position relative to said receiving means,
   e. a vacuum manifold removably carried between said separable end wall portions in spaced parallel relation above said supports and said bottom wall,
   f. recessed conically shaped seats formed in the underside of said manifold for receiving the open end of the test tube retained by said supports so as to close the same, and
   g. an evaporating needle depending from the underside of and having communication with said manifold concentrically of said recessed conically shaped seats for projection into a test tube held by said rack.

2. A multiple test tube evaporator defined by claim 1, wherein said supports comprise a pair of shelflike members and in which said means provided thereby for retaining said test tubes consist of circular openings formed in vertical alignment with respect to each other and said receiving means provided by said bottom wall.

3. A multiple test tube evaporator as defined by claim 1, wherein said means provided by said bottom wall for receiving the closed end of a test tube comprises a concave recess formed in the upper surface of said bottom wall, the bottom of which is open so as to permit drainage therethrough.

4. A multiple test tube evaporator as defined by claim 3, wherein said supports comprise a pair of shelflike members and in which said means provided thereby for retaining said test tubes consist of circular openings formed in vertical alignment with respect to each other and said concave recesses provided by said bottom wall.

5. A multiple test tube evaporator as defined by claim 1 further defined by providing means on the top edges of said end walls adapted to cooperate with means on the bottom coplanar edges of said end walls of a second rack for releasably holding the racks in a vertical stacked condition.

* * * * *